United States Patent [19]
Ebert et al.

[11] Patent Number: 5,626,866
[45] Date of Patent: May 6, 1997

[54] DRUG-CONTAINING ADHESIVE COMPOSITE TRANSDERMAL DELIVERY DEVICE

[75] Inventors: Charles D. Ebert; Srinivasan Venkateshwaran; Werner Heiber; Suresh Borsadia, all of Salt Lake City, Utah

[73] Assignee: Theratech, Inc., Salt Lake City, Utah

[21] Appl. No.: 544,110

[22] Filed: Oct. 17, 1995

Related U.S. Application Data

[63] Continuation of Ser. No. 207,786, Mar. 7, 1994, abandoned.
[51] Int. Cl.$^6$ .............................. A61F 13/00; A61F 13/02
[52] U.S. Cl. ........................... 424/447; 424/448; 424/449
[58] Field of Search .................................... 424/447, 448, 424/449

[56] References Cited

U.S. PATENT DOCUMENTS

| | | | |
|---|---|---|---|
| 4,597,961 | 7/1986 | Etscorn | 424/28 |
| 4,715,387 | 12/1987 | Rose | 131/270 |
| 4,915,950 | 4/1990 | Miranda et al. | 424/448 |
| 4,920,989 | 5/1990 | Rose et al. | 514/314 |
| 4,943,435 | 7/1990 | Baker et al. | 424/448 |
| 5,016,652 | 5/1991 | Rose et al. | 131/270 |
| 5,077,104 | 12/1991 | Hunt et al. | 428/34.3 |
| 5,110,599 | 5/1992 | Anhäuser et al. | 424/449 |
| 5,254,346 | 10/1993 | Tucker et al. | 424/449 |

Primary Examiner—Frederick Krass
Attorney, Agent, or Firm—Thorpe, North & Western, L.L.P.

[57] ABSTRACT

A method for making a transdermal drug delivery device for heat sensitive and volatile drugs is disclosed. The device contains a drug-containing adhesive composite layer having an impermeable backing material laminated to the distal surface thereof and a proximal peelable impermeable backing material adapted for removal for administering a drug to the skin or mucosa laminated to the proximal surface thereof. The method comprising the steps of providing first and second adhesive laminates each comprising a drug permeable adhesive layer having laminated to one surface one of said backing materials and having the opposing surface exposed. The drug, in gelled form and optionally containing additives such as enhancers and preservatives, is extruded onto at least one exposed surface of the first or second adhesive laminate followed by laminating together the exposed surfaces of the first and second adhesive laminate such that the adhesive layers and gelled drug are combined to form the drug-containing adhesive composite layer having the distal and proximal surfaces covered by the respective backing materials. The adhesives used in making up the laminates may be the same or different provided the drug is compatible with the adhesive. The process is particularly adaptable to the formulation of nicotine-containing patches. Drug delivery devices made according to the disclosed method and a method of using these drug delivery devices are also described.

60 Claims, 2 Drawing Sheets

DRUG-CONTAINING ADHESIVE COMPOSITE TRANSDERMAL DELIVERY DEVICE

This application is a continuation of U.S. application Ser. No. 08/207,786, filed Mar. 7, 1994, now abandoned.

BACKGROUND OF THE INVENTION

This invention relates generally to transdermal and transmucosal drug delivery (TDD) devices. More particularly, the invention relates to TDD devices for delivering heat sensitive or volatile drugs in which the drug is extruded as a gel onto an adhesive layer following which the surface of the adhesive layer onto which the gel has been extruded is laminated with a second adhesive layer to form a drug-containing adhesive composite device. Chemical enhancers for facilitating transport of the drug through the skin or mucosa and other additives can also be mixed with the drug or into the composite. Thus, the invention encompasses a method for making TDD devices using an extrusion step to incorporate a gelled drug into a dried adhesive layer, and to drug delivery devices made using the method. These methods and devices are particularly useful for delivering nicotine into the body.

Cigarette smoking is a major risk factor in coronary heart disease and is the cause of approximately 30% of all cancer deaths. However, smoking is difficult to give up, and any smoking cessation therapy has to deal with both the pharmacological and psychological dependence on cigarettes. Modest success has been obtained by separating the treatment of these two factors, such as by satisfying the pharmacological craving with nicotine pills or chewing gum while treating the psychological addiction independently.

One of the most successful approaches relies on nicotine chewing gum, which achieves direct delivery of nicotine to the systemic circulation by buccal absorption. However, nicotine chewing gum tastes bad, may lead to mouth ulcers and heartburn, and destroys dental appliances. Further, patient compliance is crucial to effectiveness. Other problems with orally administered nicotine include stomach upsets, nausea, rapid nicotine degradation, and irregular and unpredictable blood levels.

Another approach gaining increasing favor for treating the pharmacological dependence on cigarette smoking is transdermal delivery of nicotine. The skin is ordinarily a very effective barrier to passage of materials from the environment into the body. However, nicotine is very volatile, highly lipid soluble, and permeates the skin easily. For example, a comparison of average penetration rates of other transdermally administered agents through the skin show that nitroglycerin has a skin flux of 10–25 $\mu g/cm^2.h$, scopolamine 2–8 $\mu g/cm^2.h$, estradiol 0.01–0.03 $\mu g/cm^2.h$, clonidine 0.5 $\mu g/cm^2.h$, and nicotine 100–300 $\mu g/cm^2.h$. However, nicotine is also very irritating to skin and is very toxic. Therefore, development of acceptable TDD devices for delivering nicotine has required finding ways to minimize the irritation and safety problems while supplying effective doses of the substance.

A number of TDD devices for delivering nicotine have been described. Japanese Laid Open Application No. 61-251619 reports a non-controlled release device that holds low amounts of the substance and covers a relatively large area (70 $cm^2$) of skin. U.S. Pat. No. 4,597,961 to Etscorn discloses a device in which a microporous membrane minimally controls release of nicotine to the skin such that it is effective for only about 45 minutes. U.S. Pat. Nos. 4,920,989 and 5,016,652 to Rose et al. describe a nicotine patch that is preferably used with a nicotine aerosol spray that is delivered into a patient's mouth. U.S. Pat. No. 4,943,435 to Baker et al. reports a transdermal patch for delivering nicotine for periods of 12–24 hours that includes a nicotine reservoir and rate-controlling polymer matrix to regulate nicotine diffusion through the skin. U.S. Pat. No. 4,908,213 to Govil et al. discloses a transdermal nicotine patch containing an antipruritic to counteract severe itching that may occur with transdermal administration of nicotine. U.S. Patent No. 4,877,618 to Reed teaches a transdermal nicotine patch containing a stack of alternating adhesive and interlaminar layers for providing a relatively constant rate of diffusion through the skin over an extended period of time.

Methods of fabricating TDD devices have not received much attention in the patent literature. U.S. Pat. No. 4,943,435 to Baker et al. discloses a method of making a nicotine patch wherein the nicotine is preferably dissolved in an inert polymer matrix that controls the rate of nicotine release. The percentage by weight of nicotine can be varied according to the desired loading in the monolithic matrix layer, however, above about 50% nicotine by weight the polymer fails to solidify properly after casting, remaining in a gel or fluid form. Thus, this method of making nicotine patches is limited to polymers and nicotine loads that, when mixed, polymerize properly.

Another problem of drug delivery devices containing polymers and volatile drugs is that, even if polymerization is achieved in the presence of the drug, the polymer-drug combination must be allowed to dry. This is a problem for volatile drugs, such as nicotine, since the concentration of the volatile drug will diminish during drying, especially if the polymer is heated in an oven to accelerate drying. Thus, it would be advantageous to avoid fabrication methods requiring heating or drying after addition of a volatile drug to the polymer.

Baker also teaches that many of the common materials from which components of TDD devices, such as backings, adhesives, membranes, matrices, and release liners, are dissolved or degraded by nicotine. For example, Baker teaches that adhesives become stringy, lose their tackiness, or become so heavily loaded with nicotine that they deliver a huge burst of nicotine when applied to the skin. According to Baker, typical grades of polyisobutylene, acrylate, or silicone-based adhesives behave this way when exposed to nicotine for periods as little as one week. Baker further teaches that polymers that swell significantly, disintegrate, or dissolve completely in the presence of nicotine include many grades of polyvinyl chloride, polycarbonate, polystyrene, polyethylene terephthalate, polybutyrate, polyurethane, ethylene-vinyl acetate copolymers (except those with low percentages of vinyl acetate), and polyvinylidene chloride.

U.S. Pat. No. 4,915,950 to Miranda et al. describes a method for making TDD devices that involves laminating an anchor adhesive layer onto a drug-impermeable backing. Similarly, a pressure-sensitive contact adhesive is laminated onto a release liner. Then, an adsorbent source layer is deposited onto, preferably, the contact adhesive, or the anchor adhesive. A drug in liquid form is then printed onto the exposed face of the adsorbent source layer. Finally, the anchor adhesive/backing laminate is laminated onto the source/contact adhesive/release liner laminate to form the finished device. The printing step involves depositing the liquid drug onto the adsorbent source layer in a substantially uniform manner by any of a number of techniques. Use of a drug in a liquid form is a substantial problem because the drug must wet the surface of the source layer so that squeezing of liquid to the periphery of the device during lamination is substantially prevented. After deposition, the drug diffuses into one or both of the adjacent adhesive layers. Thus, the fabric material composing the source layer and its surface properties must be carefully selected so that wicking into the fabric is carefully controlled. The rate at which the liquid drug is printed onto the source layer and the subsequent lamination to the adhesive laminate,therefore, must be carefully controlled as well, which is difficult to do.

U.S. Pat. No. 5,110,599 to Anhäuser also discloses a method for producing transdermal patches through a printing process.

OBJECTS AND SUMMARY OF THE INVENTION

An object of the present invention is to provide a method of fabricating laminated TDD devices that is compatible with volatile or heat-sensitive drugs, enhancers, or other components that cannot be subjected to drying or heating, such as would occur in an oven.

Another object of the invention is to provide a method of making laminated TDD devices wherein sorption or wicking of a liquid drug formulation into a sorbent layer is not required.

A further object of the invention is to provide a method of making laminated TDD devices that permits selection and optimization of drug delivery profiles.

These and other objects may be accomplished by a method for making a TDD device comprising the steps of:

(a) providing a first adhesive laminate comprising a first drug permeable adhesive layer having laminated to one surface thereof a distal backing material and having the opposing surface exposed;

(b) providing a second adhesive laminate comprising a second adhesive layer having laminated to one surface thereof a proximal peelable release liner and having the opposing surface exposed;

(c) extruding the drug, in gel form, onto at least one exposed surface of the first or second adhesive laminate; and (d) laminating together the exposed surfaces of the first and second adhesive laminates such that the adhesive layers and gelled drug are combined to form a drug-containing adhesive composite layer having the distal backing material covering one surface thereof and the proximal peelable release liner covering the opposite surface therof.

In other words, the drug, in gel form and optionally containing enhancers, preservatives, antioxidants, anti-irritants, solubilization agents, and the like, can be extruded onto either or both of the exposed surfaces of the first or second adhesive layers which are then laminated together to form a drug-containing adhesive composite.

A further aspect of the method is protecting the exposed surfaces of both the first and second adhesive layers during fabrication of the device with in-process release liners that are removed prior to extrusion of the gelled drug onto an adhesive surface and laminating the exposed surfaces of the two adhesive layers to form the drug/adhesive composite. In this embodiment the extrusion of the gelled drug can be made on either adhesive layer followed by lamination. Furthermore, if desired, extrusion of the gelled drug could also be made on both adhesive layers.

Still another aspect, and more specific embodiment, of the method is making TDD devices for administering nicotine for smoking cessation therapy. Gelled nicotine is formulated by admixture with a gelling agent such as hydroxypropylcellulose. A preservative or antioxidant, such as butylated hydroxytoluene, can be added to the formulation as well.

DETAILED DESCRIPTION OF THE INVENTION

Figure 1:
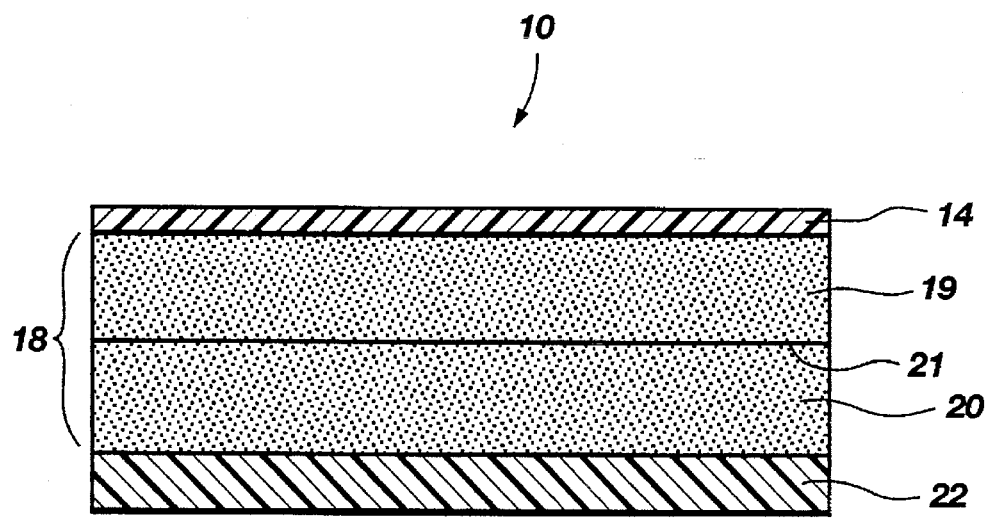
FIG. 1 shows a partly schematic, sectional view of a TDD device according to the present invention.

Before the present method of making transdermal and transmucosal drug delivery devices is disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims.

It must be noted that, as used in this specification and the appended claims, the singular forms "a," "an," and "the" include plural referents unless the content clearly dictates otherwise. Thus, for example, reference to a laminated structure containing "a drug" includes a mixture of two or more drugs, reference to "an adhesive" includes reference to two or more of such adhesives, and reference to "an enhancer" includes reference to a mixture of two or more enhancers.

In describing and claiming the present invention, the following terminology will be used in accordance with the definitions set out below.

As used herein, the term "active gel," "gelled drug," "drug in gel form," and the like means a drug in which a gelling agent is dispersed to obtain selected flow and surface tension properties for application to laminated patches. Thus, active gel is a liquid drug in a viscous yet flowable state, and can be a colloidal/biphasic or dissolved mixture of liquid drug and a gelling agent. Liquid drug means either a drug which is itself a liquid or is dissolved, suspended, or dispersed in a selected solvent or vehicle. Such a solvent could be a liquid, such as ethanol, water, and the like, or a low-viscosity semi-solid that can be extruded, such as low molecular weight polymers, waxes, petroleum jelly, and the like. Active gel may also includes enhancers that can be added to the formulation to facilitate transport of the drug through the skin or mucosa into the body. Active gel may also include a combination of drugs, gelling agents, enhancers, preservatives, antioxidants, anti-irritants, solubilization agents, and the like. The term "gel" is meant to apply to the functional nature of the thickened drug component whether or not the technical definition of a gel is met.

As used herein, the term "drug" or "pharmacologically active agent" or any other similar term means any chemical or biological material or compound suitable for transdermal or transmucosal administration by the methods previously known in the art and/or by the methods taught in the present invention, that induces a desired biological or pharmacological effect, which may include but is not limited to (1) affecting living processes, (2) having a prophylactic effect on the organism and preventing an undesired biological effect such as preventing an infection, (3) alleviating a condition caused by a disease, for example, alleviating pain or inflammation caused as a result of disease, and/or (4) either alleviating, reducing, or completely eliminating the disease from the organism. The effect may be local, such as providing for a local anaesthetic effect, or it may be systemic. This invention is not drawn to novel drugs or to new classes of active agents. Rather it is limited to devices and methods of making said devices for delivery of drugs or agents that exist in the art or that may later be established as active drugs or agents and that are suitable for delivery by the present invention. Such substances include broad classes of compounds normally delivered into the body, including through body surfaces and membranes, including skin and mucosal membranes. In general, this includes but is not limited to: antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral and cerebral; central nervous system stimulants; vasoconstrictors; cough and cold preparations, including decongestants; hormones such as estradiol and other steroids, including corticosteroids; hypnotics; immunosuppressives; muscle relaxants; parasympatholytics; psychostimulants; sedatives; tranquilizers; and nicotine and acid addition salts thereof.

The flux of a drug across the skin or mucosa can be increased by changing either the resistance (the diffusion coefficient) or the driving force (the gradient for diffusion). Similarly, the flux of an analyte (a chemical or biological material suitable for passage through a biological membrane of which an individual might want to know the concentration or activity inside the body) across the skin or mucosa for collection or analysis on the outside of the body can also be increased. Flux may be enhanced by the use of so-called penetration or chemical enhancers. Chemical enhancers are comprised of two primary categories of components, i.e., cell-envelope disordering compounds and solvents or binary systems containing both cell-envelope disordering compounds and solvents.

Cell envelope disordering compounds are known in the art as being useful in topical pharmaceutical preparations and function also in analyte withdrawal through the skin. These compounds are thought to assist in skin penetration by disordering the lipid structure of the stratum corneum cell-envelopes. A comprehensive list of these compounds is described in European Patent Application 43,738, published Jun. 13, 1982, which is incorporated herein by reference. It is believed that any cell envelope disordering compound is useful for purposes of this invention. Exemplary of the cell envelope disordering compounds are those represented by the formula:

R—X wherein R is a straight-chain alkyl of about 7 to 16 carbon atoms, a non-terminal alkenyl of about 7 to 22 carbon atoms, or a branched-chain alkyl of from about 13 to 22 carbon atoms, and X is sorbitan, glycerin, —OH, —COOCH$_3$, —COOC$_2$H$_5$, —OCOCH$_3$, —SOCH$_3$, —P (CH$_3$)$_2$O, —COOC$_2$H$_4$OC$_2$H$_4$OH, —COOCH (CHOH)$_4$CH$_2$OH, —COOCH$_2$CHOHCH3, —COOCH$_2$CH(OR")CH$_2$OR", —(OCH$_2$CH$_2$)$_m$OH, —COOR', or —CONR'$_2$ where R' is —H, —CH$_3$, —C$_2$H$_5$, —C$_3$H$_7$ or —C$_2$H$_4$OH; R" is —H, or a non-terminal alkenyl of about 7 to 22 carbon atoms; and m is 2–6; provided that when R" is an alkenyl and X is —OH or —COOH, at least one double bond is in the cis-configuration. Preferred cell envelope disordering compounds include isopropyl myristate, methyl laurate, oleic acid, oleyl alcohol, glycerol monooleate, glycerol dioleate, glycerol trioleate, glycerol monostearate, glycerol monolaurate, propylene glycol monolaurate, and sorbitan esters and mixtures thereof.

Suitable solvents include water; diols, such as propylene glycol and glycerol; mono-alcohols, such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones (azones) and the like.

U.S. Pat. 4,537,776, Cooper, issued Aug. 27, 1985, contains an excellent summary of prior art and background information detailing the use of certain binary systems for permeant enhancement. Because of the completeness of that disclosure, the information and terminology utilized therein are incorporated herein by reference.

Similarly, European Patent Application 43,738, referred to above, teaches using selected diols as solvents along with a broad category of cell-envelope disordering compounds for delivery of lipophilic pharmacologically-active compounds. Because of the detail in disclosing the cell-envelope disordering compounds and the diols, this disclosure of European Patent Application 43,738 is also incorporated herein by reference.

A binary system for enhancing metoclopramide penetration is disclosed in UK Patent Application GB 2,153,223 A, published Aug. 21, 1985, and consists of a monovalent alcohol ester of a C8-32 aliphatic monocarboxylic acid (unsaturated and/or branched if C18-32) or a C6-24 aliphatic monoalcohol (unsaturated and/or branched if C14-24) and an N-cyclic compound such as 2-pyrrolidone, N-methylpyrrolidone and the like.

Combinations of enhancers consisting of diethylene glycol monoethyl or monomethyl ether with propylene glycol monolaurate and methyl laurate are disclosed in U.S. Pat. No. 4,973,468 as enhancing the transdermal delivery of steroids such as progestogens and estrogens. A dual enhancer consisting of glycerol monolaurate and ethanol for the transdermal delivery of drugs is shown in U.S. Pat. No. 4,820,720. U.S. Pat. No. 5,006,342 lists numerous enhancers for transdermal drug administration consisting of fatty acid esters or fatty alcohol ethers of C$_2$ to C$_4$ alkanediols, where each fatty acid/alcohol portion of the ester/ether is of about 8 to 22 carbon atoms. U.S. Pat. No. 4,863,970 shows penetration-enhancing compositions for topical application comprising an active permeant contained in a penetration-enhancing vehicle containing specified amounts of one or more cell-envelope disordering compounds such as oleic acid, oleyl alcohol, and glycerol esters of oleic acid; a C$_2$ or C$_3$ alkanol and an inert diluent such as water.

Other chemical enhancers, not necessarily associated with binary systems, include DMSO or aqueous solutions of DMSO such as taught in Herschler, U.S. Pat. No. 3,551,554;

Herschler, U.S. Pat. No. 3,711,602; and Herschler, U.S. Pat. No. 3,711,606, and the azones (n-substituted-alkyl-azacycloalkyl-2-ones) such as noted in Cooper, U.S. Pat. No. 4,557,943.

Some chemical enhancer systems may possess negative side effects such as toxicity and skin irritation. U.S. Pat. No. 4,855,298 discloses compositions for reducing skin irritation caused by chemical enhancer-containing compositions having skin irritation properties with an amount of glycerin sufficient to provide an anti-irritating effect. Thus, anti-irritants can advantageously be added to drug/enhancer compositions within the scope of the invention.

The solubility of certain drugs in some adhesives used in the adhesive laminates described herein can be disadvantageously low. Solubility enhancing agents, solubilizing agents, or solubility altering agents can be added to the drug formulation to improve drug solubility and, hence, drug concentration in the adhesive laminates. Increasing the drug concentration in the adhesive laminates also increases transdermal or transdermal flux. Examples of such solubilization agents include solvents such as lower chain alcohols, diols, and triols, low molecular weight polymers such as polyethylene glycol and polypropylene glycol, and other substances suitable for increasing the solubility of the drug in the adhesive layers.

The embodiments described in FIGS. 1-4, are presented in reference to nicotine as the active drug. However, it will be apparent to one skilled in the art that any other liquid drug contained in an active gel which can be transdermally or transmucosally delivered may be substituted in place of nicotine. It is to be emphasized that the present invention is particularly adapted to the formulation of drugs, enhancers, or other ingredients of the formulation that are volatile or heat sensitive and that cannot be readily formulated under conditions where elevated temperatures are required. Since the terms "volatile" or "heat sensitive" may be considered to be relative, for purposes of definition herein drugs, enhancers, or other ingredients of the formulation are considered "volatile" or "heat sensitive" when they have a melting point, decompose or are deactivated below about 100° C., particularly below about 75° C., and most particularly below about 50° C.

Referring to FIG. 1, the TDD device provided by the present method is shown generally at 10. The device 10 is in the form of a laminated drug-containing adhesive composite layer adapted to adhere to a predetermined area of unbroken skin or mucosal tissue. The individual layers of the device 10 include a substantially drug-impermeable distal backing 14, a drug laden adhesive composite 18, which is adapted to adhere to the skin or mucosa, and a substantially drug impermeable proximal release liner 22. The adhesive composite 18 is comprised of a distal adhesive layer 19, a proximal adhesive layer 20, and a gelled drug layer 21 disposed therebetween. These layers will be described in more detail momentarily.

The distal backing layer 14, in use, defines the side of the patch that faces the environment, i.e., distal to the skin or mucosa. The functions of the backing layer 14 are to protect the patch and to provide an impenetrable layer that prevents loss of nicotine (or other liquid or volatile drug) to the environment. Thus, the material chosen should be nicotine resistant and should be minimally permeable to nicotine. Advantageously, the backing material may be opaque to protect nicotine from degradation from exposure to ultraviolet light. Further, the backing layer 14 should be capable of binding to and supporting the other layers of the device, yet should be pliable to accommodate the movements of a person using the device 10. A preferred material is polyester or aluminized polyester, for example polyester medical films such as those marketed under the tradenames Scotchpak® 1009 or 1109 from 3M Corporation. Aluminized polyester has a nicotine permeability of less than about 0.2 µg.100 µm/cm$^2$.h. There are limited materials that are sufficiently impermeable to nicotine to retain the nicotine load adequately during storage or use. However, other low permeability materials that may be used, with or without modification are those selected from the group consisting of metal foils, metalized polyfoils, composite foils or films containing polyester such as polyester terephthalate, polytetrafluoroethylene ("TEFLON®")-type materials, or equivalents thereto, polyether block amide copolymers (e.g., "PEBAX" copolymers), polyethylene methyl methacrylate block copolymers such as "NUKRELL™" polymers, polyurethanes such as "PELLATHANE™" or "ESTANE™" polymers, polyvinylidene chloride (Saran®), nylon, silicone elastomers, rubber-based polyisobutylene, styrene, styrene-butadiene and styrene-isoprene copolymers, polyethylene, and polypropylene Although many of these materials were cited by U.S. Pat. No. 4,943,435 to Baker as being unsuitable for use with nicotine, it is considered that, when formulated in the manner described herein, the listed materials are sufficiently resistant to degradation by nicotine to be useful in the presently described invention. A thickness of about 0.001 to 0.004 inch is preferred, with 0.002 to 0.003 inch more preferred.

The adhesive(s) used in forming the adhesive/drug composite 18 should be nicotine compatible and permit a useful nicotine flux. The proximal 20 and distal 19 adhesive layers play principal roles in determining the rate at which nicotine is released from the device 10. The material comprising the proximal adhesive layer 20 is a pressure-sensitive skin contact adhesive comprised of a pharmaceutically acceptable material. It should also satisfy the general criteria for adhesives used for transdermal patches including biocompatibility, ease of application, and ease of removal. The adhesives in both proximal 20 and distal 19 adhesive layers are preferably of materials in which the nicotine has moderate diffusivity. After equilibration, the substance will have diffused throughout the adhesive composite 18, which is useful for regulation of release kinetics. Thus, by careful selection of the materials used for the adhesive composite 18, the distribution of nicotine throughout the entire system can be regulated. Other useful criteria include adequate drug solubility in the adhesive layers to provide reservoir capacity. Preferably the adhesive composite 18 has a thickness in the range of about 0.001 to 0.020 inch, more preferably 0.002 to 0.010 inch, and most preferably 0.002 to 0.005 inch. Suitable adhesives for use in the practice of the invention include acrylic adhesive such as marketed under the tradenames RA2484, RA2333, RA2397, R363, and R362 from Monsanto Co.; other acrylic adhesives such as DUROTAK® 80–1196 (National Starch, crosslinked or uncrosslinked acrylic copolymer), SP18305™ (Avery International), MSX435™ (3M), and "NEOCRYL™" (Polyvinyl Chemicals, Ltd.); vinyl acetate adhesives such as Flexcryl™-1614, -1617, -1618, and -1625 from Air Products; and natural and synthetic rubbers including polyisobutylenes, neoprenes, polybutadienes, and polyisoprenes. Other suitable materials include ethylenevinylacetate copolymers, polysiloxanes, polyacrylates, polyurethanes, and plasticized weight polyether block amide copolymers ("PEBAX" copolymers). As in the case of backing materials, some of these materials were reported in U.S. Pat. No. 4,943,435 to Baker as being dissolved, attacked or degraded by nicotine, however, results indicated that, when properly formulated according to the present invention, they are suitable materials for fabricating nicotine-containing delivery devices.

The adhesives comprising the distal adhesive layer 19 and the proximal adhesive layer 20 can be the same or different. If they are different, selection of the adhesives can be used for controlling or regulating drug distribution within the adhesive composite 18. For example, if the drug is more soluble and permeable in the adhesive comprising the distal layer 19 than in the adhesive comprising the proximal layer 20, then the adhesive comprising the proximal layer 20 could be rate limiting as to diffusion of the drug out of the device 10 to the surface of the skin or mucosa. The thicknesses of the distal 19 and proximal 20 layers can also be selected to provide for desired amounts of reservoir capacity and regulation of diffusion. If the drug is more soluble and permeable in the proximal layer 20, then it is possible to provide for quick release of a selected amount of drug from the proximal layer 20 and sustained release from the distal layer 19 of a selected amount of drug over a selected period of time. Another possible arrangement is to have either the distal layer 19 or the proximal layer 20 or both be a composite. For example, if the proximal layer 20 is a composite of a proximal stratum wherein the drug is very soluble and permeable and a distal stratum wherein the drug is less soluble and permeable and the distal layer 19 is comprised of a polymer in which the drug is very soluble and permeable, the drug is released quickly from the proximal stratum of the proximal layer 20, with release from the distal layer 19 regulated by the rate limiting properties of the distal stratum of the proximal layer 20. A person skilled in the art will be able to devise other useful arrangements based on these principles.

The proximal release liner 22 covers the skin-facing or proximal side of the TDD device 10 until the device 10 is used. Therefore, the proximal release liner 22 should possess the same properties similar to those of the backing 14, and the same materials are preferred. Just prior to use of the device, the proximal release liner 22 is removed to expose the nicotine-containing adhesive composite layer 18 for contact and adhesion to the skin or mucosal surface.

As will be noted in the following description, the drug-containing adhesive 18 is actually a composite formed by bringing together two adhesive layers following deposition of the nicotine, in gel form, onto the surface of at least one of them. The adhesives forming each layer may be the same or different but must be compatible with each other and must be capable of absorbing nicotine but allowing it to diffuse from the adhesive to the skin or mucosa at an acceptable rate of flux.

Active Gel

Nicotine is a clear liquid having about the same viscosity as water. However, extrusion coating requires a viscous fluid, the viscosity influencing the coating rate and accuracy of deposition. Preferably the viscosity is in the range of about 1,000 to 200,000 centipoise, more preferably in the range of about 1,000 to 50,000 centipoise, and most preferably in the range of about 2,000 to 20,000 centipoise. To effectively extrude nicotine onto an adhesive layer in a controllable manner, such as through an extrusion slot die, the drug must be thickened to an acceptable viscosity. Hydroxypropylcellulose ("HPC"), a water soluble polymer available in pharmaceutical grade form, is a preferred gelling agent that may be added to nicotine to increase its viscosity. HPC meets the requirements of the National Formulary for heavy metal levels. HPC is added to nicotine preferably in the range of about 1–5% (w/w), more preferably in the range of about 2–4% (w/w), and most preferably in the range of about 2.5–3.5% (w/w). A particularly preferred source of HPC is Aqualon (Wilmington, Del.), which markets HPC under the tradname KLUCEL®. Other gelling agents may also be used advantageously, such as acrylic polymer thickener [AMSCO 6038A™ (Unocal)], methyl cellulose, hydroxymethyl cellulose, polyvinylpyrrolidone, polyvinyl alcohol, low molecular weight polymers, petroleum jelly, and the like.

Another trait of nicotine that can be problematic is its tendency to oxidize readily in the presence of light and air. To avoid oxidation during storage nicotine should be kept in a dark container and preferably in a dark cabinet. Flooding the storage container with an inert gas, such as nitrogen, also reduces oxidation. During fabrication of nicotine patches, oxidation is controlled by addition of an antioxidant to the active gel. A preferred antioxidant is butylated hydroxytoluene (BHT). BHT is mixed with nicotine preferably in the range of about 0.01–1.0% (w/w), more preferably in the range of about 0.03–0.3% (w/w), and most preferably in the range of about 0.05–0.2% (w/w). Other suitable antioxidants include butylated hydroxyanisole (BHA), sodium metabisulfate, maleic acid, EDTA, cysteine hydrochloride, and α-tocopherol.

Active gel is prepared by adding HPC to nicotine while stirring, taking care to avoid clumping of the gel. BHT is added and mixed with stirring, also. Then the mixture of nicotine, HPC, and BHT is tightly sealed in a container and mixed for an extended period of time to assure that the gelling agent is completely dissolved and that the mixture is homogeneous.

EXAMPLE 1

Active gel was prepared by combining 96.9% (w/w) nicotine in free base form, 3.0% (w/w) HPC (KLUCEL GF™, a low molecular weight form of HPC having a molecular weight of about 370,000), and 0.1% (w/w) BHT at room temperature. These components were mixed for 26.5 hours on a roller mill and then the active gel was stored in a nitrogen atmosphere.

Primary Intermediate Adhesive Laminate

Figure 2:
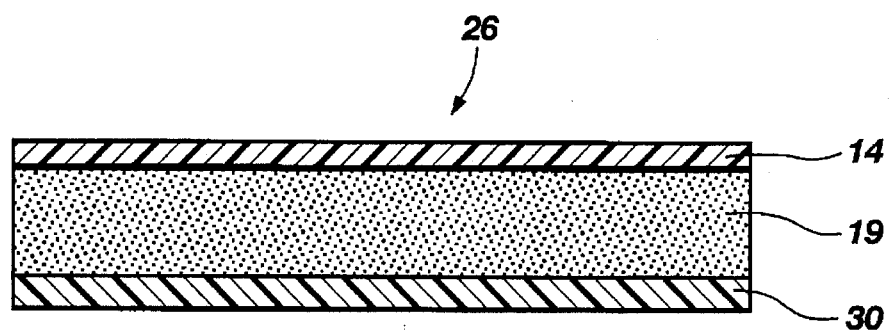
FIG. 2 shows a partly schematic, sectional view of a laminated first adhesive intermediate used in fabricating the TDD device of FIG. 1.

FIG. 2 shows a primary intermediate adhesive laminate 26 used in the process of fabricating the TDD device 10 shown in FIG. 1. This primary intermediate laminate 26 is composed of an impermeable backing 14, an adhesive layer 19, and an in-process release liner 30. The backing 14 is the same backing 14 that forms the exterior or distal covering of the TDD device, as shown in FIG. 1, and has already been described. The adhesive 19 has also been described in connection the drug loaded adhesive composite 18 of the finished device 10 of FIG. 1 and comprises the distal adhesive layer 19 in finished device 10. The thickness of the adhesive layer 19 in the primary intermediate adhesive laminate 26 is only a part or portion of the thickness of the loaded adhesive 18 composite (FIG. 1) of the device 10 once it is fabricated as a TDD since the adhesive layer 19 of the primary intermediate adhesive laminate 26 and the adhesive layer 20 of a secondary intermediate adhesive laminate 34, (described in reference to FIG. 3), are laminated together along with the gelled drug to form the drug-containing adhesive composite 18 of the device 10 (FIG. 1). In the preferred mode of manufacture, the in-process release liner 30 is laminated to the adhesive layer 19 during fabrication of the primary intermediate 26, but is removed again as part of the process for manufacturing the device 10. Under certain circumstances, however, e.g. when the adhesive layer 19 can be adequately protected, the in-process release liner 30 can be omitted from the process of TDD manufacture. The in-process release liner 30 may be composed of any of the materials described for the proximal release liner 22 of FIG. 1. However, as will be described momentarily, the inprocess release liner 30 never comes in contact with nicotine, thus it need not be made of a material that is resistant to degradation or permeation by nicotine.

The primary intermediate adhesive laminate 26 may be fabricated on a coating machine using any number of established processes. One such process is slot die extrusion wherein a thin uniform film of a casting solution is extruded onto a backing material. In a preferred embodiment of this process, the casting solution, a liquid formulation of adhesive material in an appropriate solvent, is pumped to an extrusion slot die at a controlled rate onto a release liner 30 forming a "coated web" having an exposed adhesive surface. Then the coated web or continuous roll of adhesive-coated release liner is passed through a drying oven where excess solvents are removed from the adhesive coating or layer 19. The backing film 14 is then laminated to the exposed surface of the dried cast adhesive 19 on the release liner 30 thereby completing the formation of primary laminate 26, which is then wound into roll form. Optimum coating parameters may be determined, regardless of the adhesive chosen. Full adjustability of range, casting solution flow, and drying parameters allow this process to be used in a variety of different adhesive types. The adhesive contains no drug at this point of the process. An alternative to extruding the casting solution onto the release liner 30 is extruding the casting solution onto the backing film 14.

EXAMPLE 2

A primary intermediate adhesive laminate 26 was fabricated with an acrylic adhesive coating 19. The acrylic adhesive (National Starch 80-1196) was dissolved in a solvent to form a casting solution consisting of 45% adhesive, 8.25% ethyl acetate, 25.30% isopropyl alcohol, 2.75% toluene, and 18.70% heptane. The casting solution was extruded by slot die extrusion onto a silicon polyester light release liner 30 (Release Technologies 3EST-A-S242M) on a two-zone coating/drying/laminating machine. Heating zones inside the drying oven of the machine were 80° C. and 100° C. and the line speed was set at 6 feet per minute. The dried laminate, i.e. adhesive 19 and release liner 30, was then covered with an aluminized, flesh-colored Scotchpak® 1109 (3M) backing film 14 and rewound for later use.

Secondary Intermediate Adhesive Laminate

Figure 3:
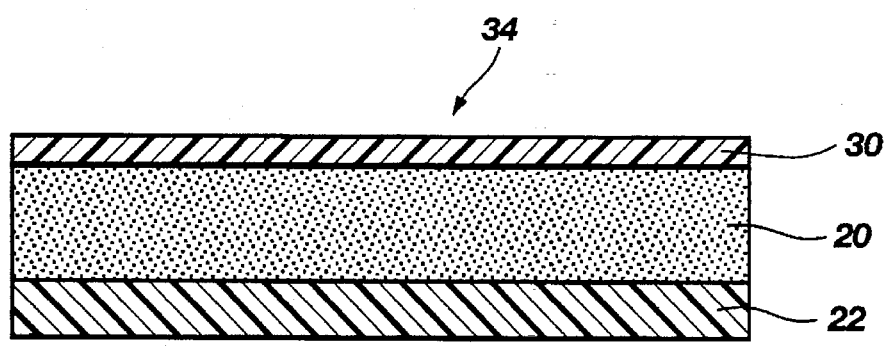
FIG. 3 shows a partly schematic, sectional view of a laminated second adhesive intermediate used in fabricating the TDD device of FIG. 1.

In FIG. 3, the secondary intermediate adhesive laminate 34 is shown to be constructed of an adhesive layer 20 laminated between an in-process release liner 30 and proximal release liner 22. All of these components have been described above. The secondary intermediate adhesive laminate 34 is manufactured in a similar manner to that of primary intermediate adhesive laminate 26. A casting solution of adhesive 20 is coated, by slot die extrusion, onto a release liner 22 and then dried. Then, instead of laminating a backing film as in the primary intermediate, an in-process release liner 30 is laminated to the adhesive-release liner structure.

Active Laminate Fabrication

Active laminate TDD 10 is fabricated from the active gel and the two intermediate laminates 26 and 34 described above. The in-process release liners 30, if present, are pulled away from each of the primary 26 and secondary 34 intermediate laminates. The gelled drug is then extruded onto the adhesive layer of either the primary 26 or secondary 34 intermediate laminate and the laminates are pressed together to join the adhesive layers 19 and 20 and gelled drug layer 21 into the adhesive composite 18. Alternatively, the gelled drug can be extruded into the lamination nip between adhesive layers 19 and 20 as they are laminated together to form the adhesive composite 18. In either procedure the result is an active laminate 10.

Figure 4:
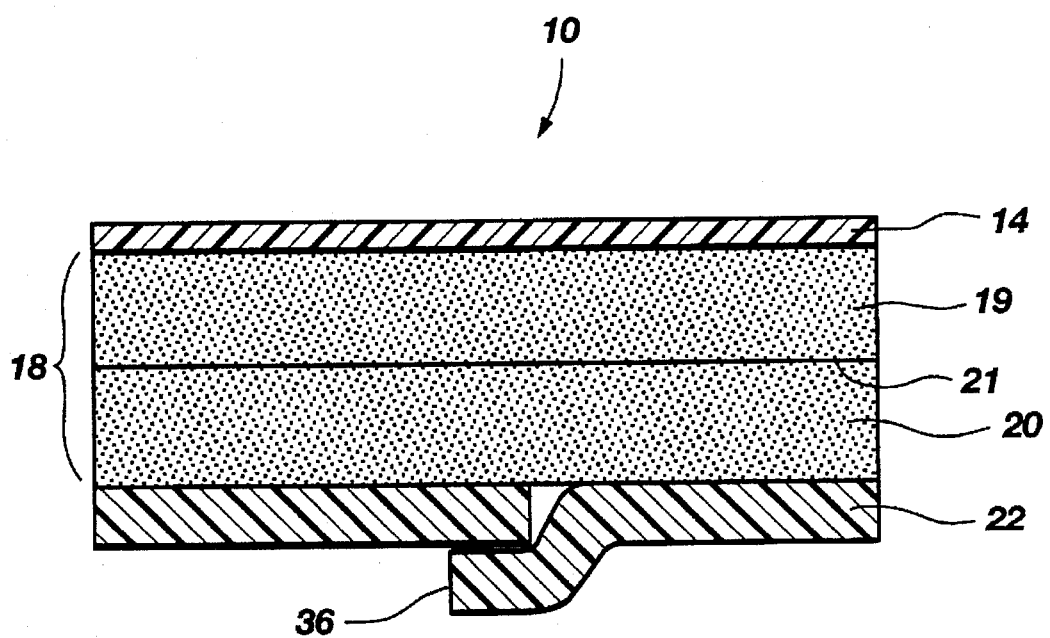
FIG. 4 shows a partly schematic, sectional view of a completed TDD device according to FIG. 1, with the addition of an overlapping proximal release liner tab.

After the active laminate 10 has been fabricated, patches are cut to the desired size and shape. Exemplary of a suitable means for this purpose is a rotary die cutter, such as a standard Webtron 650 die cutting machine. The active laminate 10 may be cut into patches of virtually any size, depending on dosage requirements. The laminate 10 is threaded onto the die cutter, where the release liner 22 covering the adhesive composite 18 is stripped off. In place of the release liner 22, narrow strips of release liner material are relaminated onto the adhesive surface. As shown in FIG. 4, the narrow strips overlap slightly to form a small tab 36 for easy peeling of the release liner upon use. The cutout pattern is generally centered over the overlap of the narrow release liner strips so that the tab 36 is centered in the patch. This type of release liner is considered equivalent to the release liner used in the initial fabrication because they both perform the same functions of protecting the adhesive layers of the TDD device and retaining the drug within the device. Thus, removing one release liner and replacing it with another is within the scope of the invention. Therefore, the term "release liner" and/or "peelable film" are intended to encompass any and all embodiments of protective liners and/or films. The resultant patches are then heat sealed in pouches.

EXAMPLE 3

Active laminate 10 was fabricated from the two intermediates 26 and 34 described previously using a coating/laminating machine. The secondary intermediate adhesive laminate 34 was fed through the machine such that the in-process release liner 30 was stripped off, exposing the distal surface of the adhesive layer 20 and release liner 22 web. Active nicotine gel was applied to the adhesive layer 20 by extrusion through a slot die. Gelled drug was pumped to the slot die and extruded onto the adhesive surface with a Zenith gear pump (0.066 ml/revolution capacity). The release liner 30 from the primary intermediate adhesive laminate 26 was stripped from the adhesive layer 19 and the remaining adhesive/backing film (19 and 14) of the primary intermediate adhesive laminate 26 was laminated onto the active gel-coated adhesive layer 20 of the secondary intermediate adhesive laminate 34 to form an adhesive composite 18. Resulting adhesive weight of the laminate sandwich was 16.2 mg/cm². Drug content of the active laminate was assayed at 1.98 mg nicotine per cm². This active laminate 10 was stored in a foil bag and protected from light to minimize drug loss.

Active laminate 10 was converted to patches and sealed in pouches as quickly as possible following fabrication of the active laminate. Release liner 22 was removed from the active laminate 10 and was replaced with narrow overlapping strips of release liner material so that tabs 36 for easy removal of the release liner 22 were formed. Active 10 cm² patches were cut from the active laminate using a rotary die cutting machine with standard die tooling. Patches were inspected after cutting and were heat sealed in polyethylene lined aluminum foil pouches. Completed patches were assayed and found to contain 1.96 mg/cm² nicotine.

EXAMPLE 4

Nicotine patches were prepared by extruding nicotine gel directly into the lamination nip while simultaneously laminating adhesive surfaces 19 and 20 together. The nicotine gel was prepared as described in Example 1 and was extruded into the lamination nip using a syringe pump at 180 mg/min. Drug loading was varied by changing the lamination line speed from 1.6 to 4.0 ft/min. The nicotine loaded adhesive laminates were then stored in foil lined bags. Patches (10 cm$^2$) were die cut using a rotary die cutter and were sealed in protective polyethylene lined foil pouches as described above. The nicotine patches were assayed for nicotine content and the results are presented in Table 1.

TABLE 1

| Laminate No. | Nicotine Concentration* (mg/g) |
| --- | --- |
| 101 | 63.64 |
| 102 | 73.77 |
| 103 | 94.15 |
| 104 | 109.06 |
| 105 | 130.90 |

*Concentration is expressed as mg nicotine per g of adhesive laminate.

EXAMPLE 5

In vitro skin flux studies were conducted using modified Franz diffusion cells. Heat separated human epidermal membrane was prepared from human cadaver whole skin by the method of Klingman and Christopher, 88 Arch. Dermatol. 702 (1963). The full thickness skin was exposed to 60° C. heat for 60 seconds, after which the stratum corneum and part of the epidermis (epidermal membrane) were gently peeled from the dermis. The epidermal membrane and nicotine patches were cut into 1 cm$_2$ pieces. After removing the proximal release liner, the exposed nicotine-containing adhesive matrix was laminated onto the stratum cormeum surface of the epidermal membrane. The skin/adhesive matrix sandwich was then placed onto the diffusion cell with the epidermal side facing the receiving compartment and clamped into place. The receiver compartment was then filled with a citrate/phosphate buffer, pH 4.0. The cell was then placed in a circulating water bath calibrated to maintain the skin surface temperature at 32°±1° C.

At predetermined time intervals, the entire contents of the receiver compartment were collected for nicotine quantitation, and the receiver compartment was refilled with fresh citrate/phosphate buffer, taking care to remove air bubbles at the skin/buffer interface. The cumulative amount of drug permeated per unit area at any time t ($Q_t$, µg/cm$^2$) was determined according to the following equation:

$$Q_t = \sum_{n=0}^{t} \frac{(C_n \times V)}{A}$$

where $C_n$ is the concentration (µg/ml) of the drug in the receiver sample of the corresponding time, V is the volume of fluid in the receiver chamber ($\approx$6.3 cm$^2$), and A is the diffusional area of the cell (0.64 cm$^2$). The slope of the best-fit straight line to the $Q_t$ v. t plot gives the steady state flux ($J_{SS}$, µg/cm$^2$/h).

In vitro skin flux results from active laminates prepared in Example 4 are presented in Table 2. Nicotine skin flux increased linearly with drug loading, as shown in FIG. 5. The equation of the line is y=−31.505+0.71447x and the coefficient of correlation is R$^2$=0.987.

TABLE 2

| Laminate No. | Nicotine Conc.* (mg/g) | In vitro Flux (µg/cm$^2$/h) | No. of Skins |
| --- | --- | --- | --- |
| 101 | 63.64 | 16.45 ± 3.99 | 2 |
| 102 | 73.77 | 20.20 ± 3.57 | 2 |
| 103 | 94.15 | 33.84 ± 5.25 | 2 |
| 104 | 109.06 | 44.61 ± 8.05 | 5 |
| 105 | 130.90 | 64.261 ± 2.74 | 5 |

*Concentration is expressed as mg nicotine per g of adhesive laminate.

EXAMPLE 6

An active albuterol laminate containing a volatile enhancer formulation was prepared using the techniques described in Example 2 and using a transparent backing film (Scotchpak 1012, 3M). The enhancer consisted of a mixture of ethanol/water/glycerol monooleate/methyl laurate/lauryl alcohol in volume ratios of 70/15/5/5/5. Albuterol free base was dissolved in the enhancer at a final concentration of 100 mg/ml. The pH was adjusted to pH 5.5 with acetic acid and the mixture was gelled with 2% HPC (Klucel GF). The active gel was extruded between adhesive layers to form an active laminate. The active laminate was immediately die cut into 5 cm$^2$ patches and sealed in polyethylene lined foil pouches. Albuterol content was assayed at 4.14±0.29 mg/patch. In vitro skin flux, determined as described in Example 5, was determined to be 0.2 µg/cm$^2$/h.

Although the above examples and description demonstrate the formation of an active nicotine laminate suitable for transdermal delivery, the same techniques can be utilized to deliver other active permeants or drugs through skin or mucosa. Therefore, the above examples are but illustrative of a complete and preferred embodiement which may be employed in operation of the present invention. The invention is directed to the discovery that the proper formulation of various volatile and/or heat sensitive drugs can be formulated into transdermal and transmucosal delivery devices for delivery to the stratum corneum or mucosa of a human or other animal. Therefore, within the guidelines presented herein, a certain amount of experimentation to obtain optimal formulations can be readily carried out by those skilled in the art. Therefore, the invention is limited in scope only by the following claims and functional equivalents thereof.

We claim:

1. A method for making a transdermal or transmucosal drug delivery device including a drug-containing adhesive composite layer consisting essentially of first and second drug permeable adhesive layers containing a drug in gel form, said composite layer having a distal backing material impermeable to said drug laminated to the distal surface of said composite layer and a proximal peelable film which is substantially impermeable to said drug and adapted for removal for administering a drug to the skin or mucosa laminated to the proximal surface of said composite layer, said method comprising the steps of:

(a) providing a first adhesive laminate comprising said first adhesive layer having laminated to one surface thereof said distal backing material and having the opposing surface of said first adhesive layer exposed;

(b) providing a second adhesive laminate comprising said second adhesive layer having laminated to one surface thereof said proximal peelable film and having the opposing surface of said second adhesive layer exposed;

(c) extruding said drug, in gel form, onto at least one exposed surface of said first or second adhesive laminate; and (d) laminating together the exposed surfaces of said first adhesive laminate and said second adhesive laminate, at least one of which contains said extruded gelled drug, such that said first and second adhesive layers and said gelled drug are combined to form said drug-containing adhesive composite layer having said distal backing material covering one surface thereof and said proximal peelable film covering the opposite surface thereof.

2. The method of claim 1 wherein the extruding of said gelled drug and said laminating together of said exposed surfaces of said laminates is a continuous process.

3. The method of claim 2 wherein the extrusion and lamination steps occur substantially simultaneously.

4. The method of claim 1 wherein said drug has a melting point, decomposes or is deactivated at a temperature below about 100° C.

5. The method of claim 4 wherein said temperature is below about 75° C.

6. The method of claim 1 wherein said drug is nicotine or an acid addition salt thereof.

7. The method of claim 6 wherein said drug is nicotine base.

8. The method of claim 1 wherein said drug is gelled by the addition of a minor amount of a member selected from the group consisting of hydroxypropylcellulose, hydroxymethylcellulose, methylcellulose and an acrylic thickener.

9. The method of claim 8 wherein the adhesive comprising said first and second adhesive layers is a member selected from the group consisting of acrylics, vinyl acetates, natural and synthetic rubbers, ethylenevinylacetate copolymers, polysiloxanes, polyacrylates, polyurethanes, polyether block amide copolymers, and mixtures thereof.

10. The method of claim 9 wherein the adhesives comprising said first and second adhesive layers are different.

11. The method of claim 10 wherein said drug has greater permeability in the adhesive comprising the first adhesive layer than in the adhesive comprising the second adhesive layer, thereby making the second adhesive layer rate limiting as to diffusion of the drug out of the device to the skin or mucosa.

12. The method of claim 10 wherein said drug has greater permeability in the adhesive comprising the second adhesive layer than in the adhesive comprising the first adhesive layer, thereby providing for quick release of the drug from the second adhesive layer and sustained release from the first adhesive layer.

13. The method of claim 10 wherein at least one of the members selected from the group consisting of the first adhesive layer and the second adhesive layer comprises a composite adhesive layer having a proximal adhesive stratum and a distal adhesive stratum in which the adhesives comprising the proximal stratum and the distal stratum have different permeabilities to said drug, thereby affecting the delivery of the drug by the device.

14. The method of claim 9 wherein the adhesives comprising said first and second adhesive layers are the same.

15. The method of claim 14 wherein said adhesive is selected from the group consisting of crosslinked and uncrosslinked acrylic copolymers.

16. The method of claim 9 wherein the gelled drug also contains an antioxidant.

17. The method of claim 3 wherein the gelled drug includes a member selected from the group consisting of penetration enhancers, anti-irritants, and solubilizing agents.

18. The method of claim 17 wherein the gelled drug includes a penetration enhancer for facilitating transport of the drug through the skin or mucosa.

19. The method of claim 18 wherein the penetration enhancer is a member selected from the group consisting of a solvent and a cell-envelope disordering compound and mixtures thereof.

20. The method of claim 19 wherein said solvent is a member selected from the group consisting of water, diols, $C_1$–$C_3$ alkanols, DMSO, dimethylformamide, N,N-dimethylacetamide, 2-pyrrolidone, N-(2-hydroxyethyl) pyrrolidone, N-methylpyrrolidone, 1-alkylazacycloheptan-2-ones and 1-arylazacycloalkyl-2-ones and the cell-envelope disordering compound is a member selected from the group consisting of isopropyl myristate, methyl laurate, oleic acid, oleyl alcohol, glycerol monooleate, glycerol dioleate, glycerol trioleate, glycerol monostearate, glycerol monolaurate, propylene glycol monolaurate and sorbitan esters.

21. A transdermal or transmucosal drug delivery device including a drug-containing adhesive composite layer consisting essentially of first and second drug permeable adhesive layers containing a drug in gel form, said composite layer having a distal backing material impermeable to said drug laminated to the distal surface of said composite layer and a proximal peelable film which is substantially impermeable to said drug adapted for removal for administering a drug to the skin or mucosa laminated to the proximal surface of said composite layer, said drug-containing adhesive composite layer being formed by a method comprising the steps of:

(a) providing a first adhesive laminate comprising said first adhesive layer having laminated to one surface thereof said distal backing material and having the opposing surface of said first adhesive layer exposed;

(b) providing a second adhesive laminate comprising said second adhesive layer having laminated to one surface thereof said proximal peelable film and having the opposing surface of said second adhesive layer exposed;

(c) extruding said drug, in gel form, onto at least one exposed surface of said first or second adhesive laminate; and (d) laminating together the exposed surfaces of said first adhesive laminate and said second adhesive laminate, at least one of which contains said extruded gelled drug, such that said first and second adhesive layers and said gelled drug are combined to form said drug containing adhesive composite layer having said distal backing material covering one surface thereof and said proximal peelable film covering the opposite surface thereof.

22. The device of claim 21 wherein the extruding of said gelled drug and said laminating together of said exposed surfaces of said laminates is a continuous process.

23. The device of claim 22 wherein the extrusion and lamination steps occur substantially simultaneously.

24. The device of claim 21 wherein said drug has a melting point, decomposes or is deactivated at a temperature below about 100° C.

25. The device of claim 24 wherein said temperature is below about 75° C.

26. The device of claim 21 wherein said drug is nicotine or an acid addition salt thereof.

27. The device of claim 26 wherein said drug is nicotine base.

28. The device of claim 21 wherein said drug is gelled by the addition of a minor amount of a member selected from the group consisting of hydroxypropylcellulose, hydroxymethylcellulose, methylcellulose and an acrylic thickener.

29. The device of claim 28 wherein the adhesive comprising said first and second adhesive layers is a member selected from the group consisting of acrylics, vinyl acetates, natural and synthetic rubbers, ethylenevinylacetate copolymers, polysiloxanes, polyacrylates, polyurethanes, polyether block amide copolymers, and mixtures thereof.

30. The device of claim 29 wherein the adhesives comprising said first and second adhesive layers are different.

31. The device of claim 30 wherein said drug has greater permeability in the adhesive comprising the first adhesive layer than in the adhesive comprising the second adhesive layer, thereby making the second adhesive layer rate limiting as to diffusion of the drug out of the device to the skin or mucosa.

32. The device of claim 30 wherein said drug has greater permeability in the adhesive comprising the second adhesive layer than in the adhesive comprising the first adhesive layer, thereby providing for quick release of the drug from the second adhesive layer and sustained release from the first adhesive layer.

33. The device of claim 30 wherein at least one of the members selected from the group consisting of the first adhesive layer and the second adhesive layer comprises a composite adhesive layer having a proximal adhesive stratum and a distal adhesive stratum in which the adhesives comprising the proximal stratum and the distal stratum have different permeabilities to said drug thereby affecting the delivery of the drug by the device.

34. The device of claim 29 wherein the adhesives comprising said first and second adhesive layers are the same.

35. The device of claim 34 wherein said adhesive is selected from the group consisting of crosslinked and uncrosslinked acrylic copolymers.

36. The device of claim 29 wherein the gelled drug also contains an antioxidant.

37. The device of claim 23 wherein the gelled drug includes a member selected from the group consisting of penetration enhancers, anti-irritants, and solubilizing agents.

38. The device of claim 37 wherein the gelled drug includes a penetration enhancer for facilitating transport of the drug through the skin or mucosa.

39. The device of claim 38 wherein the penetration enhancer is a member selected from the group consisting of a solvent and a cell-envelope disordering compound and mixtures thereof.

40. The device of claim 39 wherein said solvent is a member selected from the group consisting of water, diols, $C_1$–$C_3$ alkanols, DMSO, dimethylformamide, N,N-dimethylacetamide, 2-pyrrolidone, N-(2-hydroxyethyl)pyrrolidone, N-methylpyrrolidone, 1-alkylazacycloheptan-2-ones and 1-arylazacycloalkyl-2-ones and the cell-envelope disordering compound is a member selected from the group consisting of isopropyl myristate, methyl laurate, oleic acid, oleyl alcohol, glycerol monooleate, glycerol dioleate, glycerol trioleate, glycerol monostearate, glycerol monolaurate, propylene glycol monolaurate and sorbitan esters.

41. A method of delivering a drug through the skin or mucosa of an individual comprising;

(a) providing a transdermal or transmucosal drug delivery device including a drug-containing adhesive composite layer consisting essentially of first and second drug permeable adhesive layers containing a drug in gel form, said composite layer having a distal backing material impermeable to said drug laminated to the distal surface of said composite layer and a proximal peelable film that is substantially impermeable to said drug adapted for removal for administering a drug to the skin or mucosa laminated to the proximal surface of said composite layer, said drug-containing adhesive composite layer being formed by a method comprising the steps of:

(1) providing a first adhesive laminate comprising said first adhesive layer having laminated to one surface thereof said distal backing material and having the opposing surface of said first adhesive layer exposed;

(2) providing a second adhesive laminate comprising said second adhesive layer having laminated to one surface thereof said proximal peelable film and having the opposing surface of said second adhesive layer exposed;

(3) extruding said drug, in gel form, onto at least one exposed surface of said first or second adhesive laminate; and (4) laminating together the exposed surfaces of said first adhesive laminate and said second adhesive laminate, at least one of which contains said extruded gelled drug, such that said first and second adhesive layers and said gelled drug are combined to form said drug containing adhesive composite layer having said distal backing material covering one surface thereof and said proximal peelable film covering the opposite surface thereof;

(b) removing said proximal peelable film from said device and bringing said skin or mucosa into contact with the proximal surface of said adhesive composite layer.

42. The method of claim 41 wherein the extruding of said gelled drug and said laminating together of said exposed surfaces of said laminates is a continuous process.

43. The method of claim 42 wherein the extrusion and lamination steps occur substantially simultaneously.

44. The method of claim 41 wherein said drug has a melting point, decomposes or is deactivated at a temperature below about 100° C.

45. The method of claim 44 wherein said temperature is below about 75° C.

46. The method of claim 41 wherein said drug is nicotine or an acid addition salt thereof.

47. The method of claim 46 wherein said drug is nicotine base.

48. The method of claim 41 wherein said drug is gelled by the addition of a minor amount of a member selected from the group consisting of hydroxypropylcellulose, hydroxymethylcellulose, methylcellulose and an acrylic thickener.

49. The method of claim 48 wherein the adhesive comprising said first and second adhesive layers is a member selected from the group consisting of acrylics, vinyl acetates, natural and synthetic rubbers, ethylenevinylacetate copolymers, polysiloxanes, polyacrylates, polyurethanes, polyether block amide copolymers, and mixtures thereof.

50. The method of claim 49 wherein the adhesives comprising said first and second adhesive layers are different.

51. The method of claim 50 wherein said drug has greater permeability in the adhesive comprising the first adhesive layer than in the adhesive comprising the second adhesive layer, thereby making the second adhesive layer rate limiting as to diffusion of the drug out of the device to the skin or mucosa.

52. The method of claim 50 wherein said drug has greater permeability in the adhesive comprising the second adhesive layer than in the adhesive comprising the first adhesive layer, thereby providing for quick release of the drug from the second adhesive layer and sustained release from the first adhesive layer.

53. The method of claim 50 wherein at least one of the members selected from the group consisting of the first adhesive layer and the second adhesive layer comprises a composite adhesive layer having a proximal adhesive stratum and a distal adhesive stratum in which the adhesives comprising the proximal stratum and the distal stratum have different permeabilities to said drug thereby affecting the delivery of the drug by the device.

54. The method of claim 49 wherein the adhesives comprising said first and second adhesive layers are the same.

55. The method of claim 54 wherein said adhesive is selected from the group consisting of crosslinked and uncrosslinked acrylic copolymers.

56. The method of claim 49 wherein the gelled drug also contains an antioxidant.

57. The method of claim 43 wherein the gelled drug includes a member selected from the group consisting of penetration enhancers, anti-irritants, and solubilizing agents.

58. The method of claim 57 wherein the gelled drug includes a penetration enhancer for facilitating transport of the drug through the skin or mucosa.

59. The method of claim 58 wherein the penetration enhancer is a member selected from the group consisting of a solvent and a cell-envelope disordering compound and mixtures thereof.

60. The method of claim 59 wherein said solvent is a member selected from the group consisting of water, diols, $C_1$–$C_3$ alkanols, DMSO, dimethylformamide, N,N-dimethylacetamide, 2-pyrrolidone, N-(2-hydroxyethyl) pyrrolidone, N-methylpyrrolidone, 1-alkylazacycloheptan-2-ones and 1-arylazacycloalkyl-2-ones and the cell-envelope disordering compound is a member selected from the group consisting of isopropyl myristate, methyl laurate, oleic acid, oleyl alcohol, glycerol monooleate, glycerol dioleate, glycerol trioleate, glycerol monostearate, glycerol monolaurate, propylene glycol monolaurate and sorbitan esters.

* * * * *